US011000473B2

(12) United States Patent
Rubin et al.

(10) Patent No.: US 11,000,473 B2
(45) Date of Patent: May 11, 2021

(54) ADHESIVE ORAL DISSOLVED FILMS IN MANAGING ORAL CARE

(71) Applicant: PHARMEDICA LTD., Haifa (IL)

(72) Inventors: Yoram Rubin, Haifa (IL); David Tavor, Hod Hasharon (IL); Hock Tan, East Brunswick, NJ (US); Odeya Tairy, Chashmonaim (IL)

(73) Assignee: PHARMEDICA LTD., Haifa (IL)

( * ) Notice: Subject to any disclaimer, the term of this patent is extended or adjusted under 35 U.S.C. 154(b) by 0 days.

(21) Appl. No.: 16/323,785

(22) PCT Filed: Jul. 31, 2017

(86) PCT No.: PCT/IL2017/050845
§ 371 (c)(1),
(2) Date: Feb. 7, 2019

(87) PCT Pub. No.: WO2018/029671
PCT Pub. Date: Feb. 15, 2018

(65) Prior Publication Data
US 2019/0209458 A1 Jul. 11, 2019

(30) Foreign Application Priority Data
Aug. 8, 2016 (IL) .......................................... 247161

(51) Int. Cl.
| | | |
|---|---|---|
| A61P 29/00 | (2006.01) | |
| A61K 45/06 | (2006.01) | |
| A61K 47/38 | (2006.01) | |
| A61K 9/70 | (2006.01) | |
| A61Q 11/00 | (2006.01) | |
| A61K 9/00 | (2006.01) | |
| A61K 31/14 | (2006.01) | |
| A61K 47/36 | (2006.01) | |
| A61K 31/131 | (2006.01) | |
| A61K 6/35 | (2020.01) | |
| A61K 36/889 | (2006.01) | |
| A61K 47/32 | (2006.01) | |

(52) U.S. Cl.
CPC ................ *A61K 9/006* (2013.01); *A61K 6/35* (2020.01); *A61K 31/131* (2013.01); *A61K 31/14* (2013.01); *A61K 36/889* (2013.01); *A61K 47/32* (2013.01); *A61K 47/36* (2013.01); *A61K 47/38* (2013.01)

(58) Field of Classification Search
CPC .............. A61K 2300/00; A61K 9/2054; A61K 9/1652; A61K 9/209; A61K 9/2866; A61K 45/06; A61K 47/38; A61K 9/0056; A61K 9/006; A61K 9/7007; A61P 29/00; A61Q 11/00
See application file for complete search history.

(56) References Cited

U.S. PATENT DOCUMENTS

| | | | |
|---|---|---|---|
| 7,132,113 B2 | 11/2006 | Zerbe et al. | |
| 2006/0198873 A1* | 9/2006 | Chan ................ | A61K 9/0056 424/443 |
| 2009/0186107 A1 | 7/2009 | Haber et al. | |
| 2011/0220135 A1* | 9/2011 | Wrenn ................ | A24B 3/14 131/355 |
| 2011/0280925 A1 | 11/2011 | Tan et al. | |
| 2014/0155783 A1 | 6/2014 | Starksen et al. | |
| 2014/0377329 A1* | 12/2014 | Bryson ............. | A61F 13/00063 424/443 |
| 2015/0056268 A1* | 2/2015 | Myers .................... | A61K 47/36 424/435 |
| 2015/0202168 A1* | 7/2015 | Turkyilmaz ........... | A61K 47/28 424/400 |
| 2016/0303038 A1* | 10/2016 | Yadav .................... | A61Q 11/00 |

FOREIGN PATENT DOCUMENTS

| | | | |
|---|---|---|---|
| WO | WO-03059390 A1 * | 7/2003 | ............. A61K 9/006 |
| WO | WO2007/030754 | 3/2007 | |
| WO | WO2008/112114 | 9/2008 | |
| WO | WO2010/146601 | 12/2010 | |
| WO | WO2012/053006 | 4/2012 | |
| WO | WO2012/104834 | 8/2012 | |

(Continued)

OTHER PUBLICATIONS

Reckitt Benckiser Ireland Limited , Bonjela Oromucosal Gel, Jun. 25, 2016 [retrieved on Nov. 2, 2017] Retrieved from the Internet<URL: http://web.archive.org/web/20160625221852/http://www.medicines.ie/medicine/580/SPC/Boniela+Oromucosal+Gel>.

International Search Report for PCT Application No. PCT/IL2017/050845 dated Nov. 30, 2017.

Zulfakar, Mohd Hanif; Goh, Jing Yi; Rehman, Khurram. Development and mechanical characterization of eugenol—cetalkonium chloride sustained release mucoadhesive oral film. Polymer Composites, 2016, 37.11: 3200-3209.

Extended European Search Report for EP Application 17838919.30 dated Jun. 7, 2019.

Office Action for IL Application No. 247161 dated Dec. 23, 2018.

(Continued)

*Primary Examiner* — Tracy Liu
(74) *Attorney, Agent, or Firm* — Pearl Cohen Zedek Latzer Baratz LLP

(57) ABSTRACT

Disclosed is a dissolvable film adapted to adhere to an oral mucosal tissue of a subject, wherein the film comprises at least three indigestible hydrophilic polymers constituting from 35% to 55% of the film dry weight and wherein the at least three polymers comprise xanthan gum and carboxymethyl cellulose (CMC) in a weight ratio of between 1:0.8-1.6, and at least one other cellulose based polymer. Optionally, the film may further include an active agent in an amount of 0.01% to 35% of the film dry weight. Disclosed also is a method for preparing the film and a method for treating or preventing oral conditions comprising implementing the film. Particularly, the film may be applied between dentures and the gums of the user.

5 Claims, No Drawings

(56) References Cited

FOREIGN PATENT DOCUMENTS

WO    WO2013/171146    11/2013
WO    WO2016/105439    6/2016

OTHER PUBLICATIONS

Bala, Rajni, et al. Orally dissolving strips: A new approach to oral drug delivery system. International journal of pharmaceutical investigation, 2013, 3.2: 67.
Office Action for IL Application No. 264747 dated Feb. 11, 2020.

* cited by examiner

ADHESIVE ORAL DISSOLVED FILMS IN MANAGING ORAL CARE

CROSS-REFERENCE TO RELATED APPLICATIONS

This application is a National Phase Application of PCT International Application No. PCT/IL2017/050845, International Filing Date Jul. 31, 2017, published as WO 2018/029671, claiming priority from IL Application No. 247161, filed on Aug. 8, 2016, which are hereby incorporated by reference.

FIELD OF THE INVENTION

The invention relates to oral film-shaped formulations for administration of agents efficient in managing various oral conditions, including halitosis, dry mouth, as well as various conditions associated with the dentures.

BACKGROUND OF THE INVENTION

There are many conditions, including oral conditions that may be treated with tablets, capsules, and lozenges containing active agents, wherein masticating and/or licking the objects freely moving in the mouth may release active agents affecting the treated conditions. Halitosis and dry mouth are examples of conditions that are difficult to handle, and a need is felt for means that would not require incessant chewing and sucking.

WO 2012/104834 discloses an oral film for slow release of insulin in mouth, the film consisting of a plurality of polymeric materials being arranged into two or more distinct layers. U.S. Pat. No. 7,132,113 discloses a breath-freshening film containing hydroxypropyl cellulose and starch, wherein the starch was found to be essential for the film properties. However, starch can be decomposed by mouth enzymes, producing lower sugars that can feed undesired microorganisms. However, U.S. Pat. No. 7,132,113 discloses a film that dissolves within one minute and therefore, is extremely limited in its potential applications.

SUMMARY OF THE INVENTION

In view of the disadvantages detailed above, a mucosal adhesive oral film for continual release of an active agent would be helpful. It is therefore an object of this invention to provide a mucoadhesive film for placing into oral cavity, and releasing agents for treating oral conditions without need to masticate or chew.

It is another object of this invention to provide a film for continual release of active agents in the oral cavity, without using starch or other materials producing lower sugars in the mouth cavity.

It is yet another object of this invention to provide an adhesive film for placing on the mouth mucosa, which dissolves within one to eight hours and releases a therapeutic dose of the desired active agent.

It is a further object of this invention to provide a thin film which is strong and elastic, and exhibits a smooth surface.

This invention also aims at providing a film for effectively treating or preventing mouth conditions, the conditions including halitosis, dry mouth, and denture problems.

This invention further provides a film for preventing sores caused by ill-fitting dentures.

Embodiments of the invention include a dissolvable film adapted to adhere to an oral mucosal tissue of a subject, wherein the film comprises i) at least three indigestible hydrophilic polymers constituting from 35% to 55% of the film dry weight; ii) an active agent released from the film within eight hours or more for treating or preventing an oral condition, constituting from 1% to 35% of the film dry weight; wherein the at least three polymers comprise xanthan gum and carboxymethyl cellulose (CMC) in a weight ratio of about 1:1, and at least one other cellulose-based polymer. In some embodiments, the xanthan gum and CMC constitute from 15% to 25% of the film dry weight. The other cellulose-based polymer is hydroxypropyl methylcellulose (HPMC). In one embodiment, the film of the invention comprises xanthan gum, CMC, and HPMC in a weight ratio of about 1:1:2.5. The film of the invention further comprises plasticizers in an amount of from 15% to 50% of the film dry weight, and one or more additives in an amount of from 0% to 4% of the film dry weight, the additive being selected from the group consisting of additional active agents, polymers adjusting the hydrophobicity of the polymer structure of the film, plasticizers, sweeteners, taste-masking agents, taste or flavor modifiers, release modifiers, permeation enhancers, pH-adjusting agents or buffering agents, preservatives or stabilizers, complexing agents, coloring agents, emulsifying agents, solvents selected from water, acetone, and alcohols, and inert fillers. In one embodiment of the invention, the film further comprises a polyacrylic acid (PA) based polymer, such as for example Carbopol. Compared to the cellulose-based polymers, these PA-based polymers are relatively less hydrophilic (more hydrophobic) and exhibit different interactions, they are also less bulky and less hydrated; this may be employed for incorporating various components and active agents into the film structure in the desired way. The film may be advantageously employed for managing oral conditions, for example oral condition selected from the group consisting of herpetic gingivostomatitis, aphthous stomatitis, irritation fibroma, swollen floor of mouth, enlargement of tongue, glossitis, oral erythema, salivary glands swelling, dry mouth, xerostomia, gingivitis, denture sores, sore throat, and many others conditions that may benefit from controlled release of an agent in the mouth cavity within 8 hours or more. The film of the invention may comprise additional active agents, such as agents being selected from the group consisting of additional breath fresheners, anti-cavity compounds, anti-anxiety agents, anti-inflammatory agents, analgesics, anti-histamines, local anesthetics, anti-bacterial compounds, disinfectants, antiseptics, antibiotics, anti-fungals, anti-migraine, anti-asthmatics, cold remedies, cough remedies, nicotine, proton pump inhibitors, H2 receptor antagonists, vitamins and other dietary and nutritional supplements. The film of the invention may exhibit a smooth surface. According to some embodiments, both surfaces of the thin film are identical. The film may have a thickness of up to 0.8 mm. According to some embodiments, the film has a thickness of up to 0.3 mm, such as up to 280 µm, for example up to 270 µm, for example up to 260 µm, for example up to 250 µm, for example up to 240 µm, for example up to 230 µm, for example up to 220 µm, for example up to 210 µm. The film of the invention may have a thickness of up to 200 µm, for example about 200 µm, or up to 190 µm. The terms "dissolvable" or "erodible" as used herein are interchangeable, unless specifically mentioned otherwise or unless a person skilled in the art would have understood those terms to have different meanings in specific instances. The terms "dissolvable" and "erodible" may be used to describe a film that dissolves in the mouth cavity, or that decomposes while its components are essentially dissolved or removed from the mouth cavity within the desired time.

Some embodiments of the invention are directed to a method for delivering an active agent to a subject, comprising applying a film to a mucosal tissue in the mouth, wherein the film comprises at least three indigestible hydrophilic polymers constituting from 35% to 55% of the film dry weight and the active agent in an amount of from 1% to 35% of the film dry weight; wherein the active agent is released from the film within 8 hours or more and mitigates an oral pathological condition in the subject, and wherein the at least three polymers comprise xanthan gum and carboxymethyl cellulose (CMC) in a weight ratio of about 1:1, and at least one other cellulose-based polymer. According to some embodiments, the tissue may comprise buccal mucosa, palate mucosa, sublingual mucosa, or gingival tissues.

Some embodiments of the invention are directed to a method for preparing a thin flexible polymeric film for adhering to a mouth mucosa or gingival tissue, and for releasing within 8 hours or more a therapeutic or other agent to the mouth cavity or to the mouth mucosa, the film not feeling unpleasant in mouth and being dissolved within the 8 hours or more, the method comprising the steps of i) providing at least three indigestible hydrophilic polymers in amounts constituting from 35% to 55% of the film dry weight, wherein the at least three polymers comprise xanthan gum and CMC in a weight ratio of about 1:1, and at least one other cellulose-based polymer; providing plasticizers in an amount of from 15% to 50% of the film dry weight, ii) providing desired active agent(s) in an amount corresponding to from 1% to 35% of the film dry weight, and desired additives in an amount of from 0% to 4% of the film dry weight; iii) mixing the polymers, the plasticizers, and water soluble agents and additives with water or aqueous solvent, thereby obtaining an aqueous phase; iv) mixing the agents and additives that are insoluble in water, if there are any, with a hydrophilic organic solvent, thereby obtaining an organic phase; v) adding the aqueous phase to the organic phase, if there is any, thereby obtaining a hydrated homogeneous polymer gel; vi) die-casting the gel on a plastic liner and drying, thereby obtaining a film substrate; vii) cutting the substrate to film pieces of the desired size and shape, and packaging. The aqueous solvent in step iii) may comprise water, alcohols, and acetone, or mixtures thereof. The organic solvent in step iv) may comprise alcohols, acetone, or mixtures thereof. The drying in step vi) may comprise drying at ambient conditions, for example allowing to spontaneously dry, aiming at residual water content of typically 12 wt % or less, such as about 10 wt % or less.

The permeation enhancer may comprise Brij 58, Brij 35, sodium glycocholate, and others. The flavorant may comprise, for example, peppermint oil, strawberry flavor, saccharin, and others.

Some embodiments of the invention are directed to a dissolvable film adapted to adhere to an oral mucosal tissue of a subject, wherein the film comprises:
  i) at least three indigestible hydrophilic polymers constituting from 35% to 55% of the film dry weight; and optionally
  ii) an active agent 0.01% to 35% of the film dry weight; wherein the at least three polymers comprise xanthan gum and carboxymethyl cellulose (CMC) in a weight ratio of between 1:0.8-1.6, and at least one other cellulose-based polymer.

According to some embodiments, the xanthan gum and CMC constitute from 15% to 25% of the film dry weight.

According to some embodiments, the at least one other cellulose-based polymer is hydroxypropyl methylcellulose.

According to some embodiments, the film of the invention further comprises plasticizers in an amount of from 25% to 50% of the film dry weight. According to some embodiments, the film of the invention further comprises an additive in an amount of up to 4% of the film dry weight, the additive being selected from the group consisting of additional active agents, polymers adjusting the hydrophobicity of the polymer structure of said film, permeation enhancers, sweeteners, taste-masking agents, taste or flavor modifiers, plasticizers, release modifiers, pH-adjusting agents or buffering agents, preservatives or stabilizers, complexing agents, coloring agents, emulsifying agents, solvents selected from water, acetone, a alcohols, and inert fillers. According to some embodiments, the film of the invention further comprises a polyacrylic acid based polymer.

According to some embodiments, the film of the invention comprises between 4.0-5.0 mg choline salicylate and between 0.03-0.07 mg cetalkonium chloride.

According to some embodiments, the active agents are selected from the group consisting of a breath freshener, an anti-cavity compound, an anti-anxiety agent, an anti-inflammatory agent, an analgesic, an antihistamine, a local anesthetic, an anti-bacterial compound, a disinfectant, an antiseptic, an antibiotic, an anti-fungal, an anti-migraine, an anti-asthmatic, a cold remedy, a cough remedy, nicotine, a proton pump inhibitor, a H2 receptor antagonist, a vitamin, a dietary supplement, a nutritional supplement or any combination thereof.

According to some embodiments, the active agents are selected from oils, menthol containing additives, polymers or any combination thereof. According to some embodiments, the active agent is coconut oil.

According to some embodiments, the film of the invention has a thickness of up to 0.8 mm.

Further embodiments of the invention are directed to a method for delivering an active agent to a patient, comprising applying the film of the invention, as detailed herein, to a mucosal tissue. According to some embodiments, the mucosal tissue comprises buccal mucosa, palate mucosa, sublingual mucosa, or gingival mucosa.

Further embodiments of the invention are directed to a method for preparing the films of the invention, wherein the method comprises the steps of:
  i) providing at least three indigestible hydrophilic polymers in amounts constituting from 35% to 55% of the film dry weight with water, wherein said at least three polymers comprise xanthan gum and CMC in a weight ratio of between 1:0.8-1.6, and at least one other cellulose-based polymer; providing plasticizers in an amount of from 20% to 50% of the film dry weight,
  ii) optionally providing desired active agent(s) in an amount corresponding to from 0.01% to 35% of the film dry weight, and desired additives in an amount of from 0% to 4% of the film dry weight, wherein said agents and said additives may be water soluble or insoluble;
  iii) mixing the polymers, the plasticizers, and optionally said active agents and additives which are water soluble with water or aqueous solvent, thereby obtaining a homogeneous aqueous phase;
  iv) mixing said active agents and additives which are insoluble in water, if there are any, with a hydrophilic organic solvent, thereby obtaining a homogeneous organic phase;

v) adding said aqueous phase to said organic phase, if there is any, thereby obtaining a hydrated homogeneous mixture; and vi) die-casting said aqueous phase of step iii) or said hydrated mixture of step v) on a plastic liner and drying, whereby obtaining a film substrate.

According to some embodiments, the aqueous solvent in step iii) comprises water mixed with an alcohol, acetone, or mixtures thereof; and wherein said organic solvent in step iv) comprises an alcohol, acetone, or mixtures thereof.

According to some embodiments, the drying in step vi) comprises allowing to dry at ambient conditions, until the residual water content is up to 10 wt %.

Further embodiments of the invention are directed to a dissolvable film adapted to be applied between a denture and gum, wherein the film comprises 35-55% w/w of three indigestible hydrophilic polymers, including xanthan gum and CMC in a weight ratio of between 1:0.8-1.6, and at least one other cellulose-based polymer. The film may further comprise an active agent as hereinafter defined and any other agent as suggested herein.

According to some embodiments, the dissolvable film adapted to be applied between a denture and gum further comprises an active agent in an amount of 0.01% to 35% of the dry weight of the film. According to some embodiments, the active agent is selected from choline salicylate, cetalkonium chloride and any combination thereof.

Further embodiments of the invention are directed to a method for reducing or preventing friction between a denture and gum, wherein the method comprises applying the dissolvable film of the invention between the gum and the denture.

Additional embodiments of the invention are directed to a method for preparing a dissolvable film adapted to be applied between a denture and gum, wherein the method comprises:

i) providing at least three indigestible hydrophilic polymers in amounts constituting from 35% to 55% of the film dry weight with water, wherein said at least three polymers comprise xanthan gum and CMC in a weight ratio of between 1:0.8-1.6, and at least one other cellulose-based polymer; providing plasticizers in an amount of from 20% to 50% of the film dry weight, ii) providing desired additives in an amount of from 0% to 4% of the film dry weight, wherein said additives may be water soluble or insoluble; iii) mixing the polymers, the plasticizers, and additives which are water soluble with water or aqueous solvent, thereby obtaining a homogeneous aqueous phase;

iv) mixing said additives which are insoluble in water, if there are any, with a hydrophilic organic solvent, thereby obtaining a homogeneous organic phase;

v) adding said aqueous phase to said organic phase, if there is any, thereby obtaining a hydrated homogeneous mixture; and vi) die-casting said aqueous phase of step iii) or said hydrated mixture of step v) on a plastic liner and drying, whereby obtaining a film substrate.

According to some embodiments, step (ii) further includes providing desired active agent(s) in an amount corresponding to from 0.01% to 35% of the film dry weight and wherein steps (iii) and (iv) further comprise mixing the active agent(s) together with the additives. According to some embodiments, the aqueous solvent in step iii) comprises water mixed with an alcohol, acetone, or mixtures thereof; and wherein said organic solvent in step iv) comprises an alcohol, acetone, or mixtures thereof. According to some embodiments, the drying in step vi) comprises allowing to dry at ambient conditions, until the residual water content is up to 10 wt %.

Further embodiments of the invention are directed to a method for treating or preventing an oral condition, wherein the method comprises administering the dissolvable film of the invention and wherein the oral condition is selected from the group consisting of herpetic gingivostomatitis, aphthous stomatitis, irritation fibroma, swollen floor of mouth, enlargement of tongue, glossitis, oral erythema, salivary glands swelling, dry mouth, xerostomia, halitosis, gingivitis, denture sores, sore throat.

DETAILED DESCRIPTION OF THE INVENTION

It is noted that throughout, all ranges and numeric figures are considered to be approximate even when the term "about" is not used, such that the document is considered to cover ±10% of the disclosed range or figure, unless specifically mentioned otherwise. It is further noted that the term "about" is also considered to cover ±10% of the disclosed range or figure, unless specifically mentioned otherwise.

It is further noted that throughout, the term "active agent" and the like, such as "active ingredient" are defined to include any agent that provides a desired therapeutic effect. Thus, any natural or chemical agents that provide a desired therapeutic effect, such as sensational comfort when applying dentures, relieving bad breath, stimulating saliva formation and the like, are included in the term "active agent". For example, not only pharmaceutically known active agent are included; also any type of polymer, oil, such as coconut oil, which may relive friction caused by dentures and may and therefore relieve pain, falvoring, such as FC bright flavor, which contains menthol and may aid in controlling bad breath, and the like are included in the definition of "active agent" as used herein.

The invention is based on the finding that a tripolymer formulation comprising xanthan gum and CMC in a weight ratio of between about 1:0.8-1.6, e.g. 1:0.8, 1:1, 1:1.2, 1:1.4, or 1:1.6, together with at least one other cellulose-based polymer provides a simple means for obtaining a thin, flexible, smooth film with a high load of active agent, e.g., up to 35% active agent. In some embodiments, the tripolymer formulation of the invention is devoid of an unpleasant feeling in mouth. In some embodiments, the tripolymer formulation of the invention does not release low sugars in the mouth. The tripolymer formulation may, for example, contain xanthan gum, CMC, and HPMC in a weight ratio of about 1:0.8-1.5:2.0-3.0 for the three components. In some embodiments, the tripolymer formulation is further combined with plasticizers, such as PEG with or without propyleneglycol. According to some embodiments, the amount of the plasticizers may be between about 15-50% w/w. According to some embodiments, the weight of the plasticizers may be up to about the combined weight of the three polymers. According to some embodiments, such a mixture enables the easy incorporation of a desired active agent in an amount of up to about 2%, 5%, 10%, 15%, 20%, 25% 30% or 35% followed by casting a thin film. The dissolvable film exhibits dissolving time of up to 8 hours or more, the time can be tuned by increasing or decreasing the amounts of additives; for example, admixing polymers that are relatively more hydrophobic, affects the release rate of the active agent. In one embodiment of the invention, the release rate is regulated by the amount of added poly acrylic acid (PA)-based polymers, for example crosslinked PA such as carbopol; the amount of carbopol may be up to 4 wt % of the film dry weight. In one embodiment, films with a high load of the active agent, e.g., up to about 35% were prepared, usually comprising up to 10 wt % water after drying, which is ready for being applied onto the mouth mucosa where it is rehydrated in situ. The dehydrated films may be stored for prolonged periods, such as for several months up to 5 years, according to the character of the active agent and according to the storage temperature.

The invention provides a film for adhering onto the oral mucosa and for releasing mitigating or healing agents, the film consisting of (per dry weight) 45±10 wt % of three indigestible polymers comprising xanthan gum, CMC, and another cellulose-based polymer; 18±17 wt % active agent(s); 35±15 wt % plasticizers; and 2±2 wt % additives. According to some embodiments, xanthan and CMC are in a weight ratio of between about 1:0.8-1.6, e.g., about 1:0.8, 1:1, 1:1.2, 1:1.4, 1:1.6. According to some embodiments, the plasticizers comprise PEG, propylene glycol or any combination thereof. According to some embodiments, at least one of the cellulose based polymers had mucuadhesive properties and therefore, allows the film to adhere to the mucus membranes.

The three polymers used in the tripolymer formulation of the invention may be suitable for the purpose of continual dissolution and release of the active agent on the mouth mucosa, possibly due to mutually compatible molecular structures resulting in strong attraction forces between the polymeric chains that are combined in the gel, such that the gel is stable and has advantageous physical properties, resulting in thin compressed films, which are smooth and semi-transparent. The films according to the inventions were compared with films prepared according to previously known techniques, and their smoother texture was observable by eye and felt by fingers. In contrast to various gels employing starch, the instant film, which does not include starch, is not cleaved by the enzymes produced in the mammalian mouth. The cellulose chains are well miscible with water and ethanol, which are the most commonly approved solvents for preparation of biomedical films, and this also contributes to the ease and cost effectiveness of the process according to the invention. The films may last, for example, for from 1 to 8 hours until they fully dissolve in the mouth.

In one embodiment, the film according to the invention is employed for supporting dentures and/or preventing and/or reducing friction between the denture and gums or any other part of the mouth. The hydrated polymeric film acts as a barrier suppressing the high load thus reducing the pressure of the denture on the gums. According to some embodiments, the film includes an active ingredient, e.g., analgesics and/or antiseptics, to prevent and/relieve pain and/or infections. According to some embodiments, the film does not include active ingredients, and therefore, act only as a physical barrier preventing friction between the dentures and the gums. This may be essential especially upon the initial use of the dentures.

According to some embodiments, the films of the invention, with or without added active ingredients, may be used for supporting any type of denture or the like and/or for preventing and/or reducing the friction between any type of denture and the gums or any other part of the mouth. For example the dentures may be local dentures used to replace a limited number of teeth, full mouth dentures, replacing an entire set of teeth, the upper teeth and/or the lower teeth. According to further embodiments, the films may prevent friction of any type of orthodontic treatments, including any type of relevant oral treatment. According to some embodiments, the films of the invention may be implemented and replaced with new films by the patient as desired, with no medical assistance, e.g., when friction is experienced. According to some embodiments, the films of the invention may be implemented/replaced in any desired frequency, e.g., once an hour, once a day, once every eight hours, once every twelve hours, once a week, once every other day, and the like. According to some embodiments, the frequency in which the films of the invention are implemented/replaced is determined by the patient, who may, according to oral sensation, implement/replace the film, as desired.

According to some embodiments, an active agent is added by reducing the amount of matrix forming polymers, by reducing the amount of plasticizers or both. According to some embodiments, the active ingredient added to the film is an analgesic selected from choline salicylate, benzocaine, camphor, carbamide peroxide, benzalkonium chloride, menthol, zinc chloride, glycerin, liquified phenol, sodium carbonate, sodium borate, docosanol, allantoin, white petrolatum, dimethicone, pramoxine hydrochloride, methyl antranilate, octyl methoxycinnamate, octyl salicylate, oxybenzone, dyclonine hydrochloride, zinc oxide, benzyl alcohol, or any combination thereof.

According to some embodiments, the amount of the choline salicylate in the film is between about 8.5-9.0% w/w, approximately about 8.7% w/w. According to some embodiments, the active ingredient added to the film is an antiseptic selected from cetalkonium chloride, povidone-iodine, sodium hypochlorite, chlorhexidine, or any combination thereof.

According to some embodiments, the amount of the cetalkonium chloride is not more than 0.01% w/w. According to some embodiments, the amount of the cetalkonium chloride is between about 0.001-0.01% w/w. According to some embodiments, the film comprises both about 8.7% w/w choline sacylate and about 0.01% w/w cetalkonium chloride. According to some embodiments, the film comprises both about 8.5-9.0% w/w choline salicylate and about 0.001-0.01% w/w cetalkonium chloride.

In another embodiment, the film of the invention is loaded with agents effectively managing halitosis, including agents such as menthol. In a still other embodiment, the film of the invention is adjusted to release agents that affect dry mouth or xerostomia, for example coconut oil, or plant extracts, or commercial ingredients such as, for example, Optaflow. According to some embodiments, the film structural components, e.g. CMC and xanthan gum, may support mouth moisture induction and saliva stimulation.

The oral film of the invention may enable the release of an active agent into the oral mucosa or to the mouth. The films may be applied buccally, palately, sublingually, or gingivally. The oral film may be in any shape or form (such as square, rectangular, circular, oval, etc.). According to some embodiments, the film is between about 0.1-0.3 mm thick. Many different sizes can be employed. Illustrative film areas (e.g., length×width) include 25 cm2 or less and 5 cm2 or more. According to some embodiments, the films may be cut to any shape and/or size in order to fit the treated area. For example, when used for preventing friction between dentures and the gums, the film applied may be cut to specifically fit between the dentures and the gums.

In a further aspect of the invention, the oral film may contain additional active agents to be released into the oral cavity. An "active agent" includes cosmetically or pharmacologically active agents, such as tooth desensitizing agents, additional breath fresheners, anti-cavity compounds, anti-anxiety agents, anti-oxidants, anti-inflammatory agents, analgesics, antihistamines, local anesthetics, anti-bacterial compounds, disinfectants, antibiotics, anti-fungals, anti-migraine, anti-asthmatics, cold remedies, cough remedies, nicotine, proton pump inhibitors, H2 receptor antagonists, vitamins and other dietary and nutritional supplements.

The thin film may be applied to the oral cavity and may adhere to a mucosal surface, such as the cheek or palate, where the film disintegrates and releases the agents for absorption through the oral mucosa or for acting inside the mouth cavity. Absorption through oral mucosa may have a role, for example, in using denture-supporting films of the invention releasing small molecules such as choline salicylate and cetalkonium chloride. In other applications of the oral film according to the invention, such as films for managing halitosis and dry mouth, the action inside the mouth cavity may be more relevant. The release of the agents from the thin film occurs without mastication, such as chewing or sucking of the film, and there is no risk of choking or swallowing the whole dosage form, which may occur with tablets, capsules or lozenges. The polymers constituting the film are indigestible, do not decompose to lower sugars, and do not feed undesired bacteria in the mouth cavity. The composition of the oral film may begin to dissolve quickly in the oral cavity. In some embodiments the composition may begin to dissolve within about 30 seconds, and may still remain active in some films for up to about 8 hours. According to some embodiments, the dissolving rate of the film may be controlled by changing the matrix polymer and/or carbopol content. According to some embodiments, the increase of the matrix polymer content and/or the carbopol content lengthens the time before the dissolution of the film. According to one embodiment of the invention, the oral film-shaped of the invention is characterized in that the active agent constitutes about 0.01 wt % of the film or more, such as 0.05 wt % or more, for example 0.1 wt % or more, 1.0 wt % or more, 5.0 wt % or more, 10 wt % or more, or 15 wt % or more, or 20 wt % or more, or 25 wt % or more or 30 wt % or more or 35 wt % or more.

In one embodiment of the invention, the film is a single-layer simple film. According to other embodiments, the film may be employed as a part of a multilayer system when required. The film of the invention may be suitable for transmucosal administration of the active agent(s) contained therein, for example buccal, or for releasing the agent into the mouth cavity. According to one embodiment, the film of the invention is characterized in that it is mucoadhesive. According to some embodiments, both surfaces have the same or similar mucoadhesive features.

Suitable cellulose derivatives for employing in the films of the invention include alkyl celluloses, such as methyl cellulose and ethyl cellulose, substituted alkyl celluloses, such as hydroxyethyl cellulose, hydroxypropyl cellulose, hydroxypropyl methylcellulose, salts of substituted alkyl celluloses, and mixtures thereof. Plasticizers suitable for use in the film of the invention may include propylene glycol, glycerin, PEG-4000, PEG-400, and the like. Plasticizers may have surfactant properties, and they may act as release modifiers, e.g. non-ionic detergents such as Brij 35 (polyoxyethylene (35) lauryl ether), Brij 58 (polyoxyethylene (20) acetyl ether), and the like. Plasticizers impart flexibility to the dosage forms, and can affect the release profile of the active agent(s) therein. PA-based polymers suitable for admixing into the film of the invention include, for example, acrylic acid copolymers, methacrylic acid polymers, methacrylic acid copolymers, cross-linked polyacrylic acid, such as Carbopol, which is PA crosslinked with polyalkenyl ethers or divinyl glycol, examples of such Carbopols being Carbopol 971, Carbopol 974. and Carbopol 1342.

The film-shaped preparation of the invention is introduced into the oral cavity (e.g. buccal, sublingual, palatal, gingival) and adheres to the mucosa. Film application may be repeated as often as required, e.g. every 8 h or 24 h. According to some embodiments, the application of a new film is performed as required by the patient, according to the sensation in the mouth of the patient.

In specific embodiments, the film of the invention is stable at 4° C., or even at room temperature. In situ, the oral film typically maintains its integrity at least partially, which may be demonstrated in vitro, while imitating the human saliva solution and exposing the film for several hours, up to 8 h.

The following examples are set forth to further illustrate the oral films of the invention. The below examples, however, should not be construed as limiting the present invention in any manner.

EXAMPLES

The solvent-casting method was used for fabricating thin polymeric matrix films.

Drug dissolution tests were conducted by placing the film (a 2.3 cm×2.3 cm unit dose) in an agitated (at 100 rpm) bottle containing 100 mL USP phosphate buffer (pH 6.8) at 37° C. Typically, samples were withdrawn at 5 min, 15 min, 30 min, 1 h, 1.5 h, 2 h, 4 h, 8 h for assay for the agent.

To enable in vitro study of agent release, the films were applied onto EpiOral tissues (MatTek) according to the Drug Absorption Protocol (ORL-202 & ORL-606). EpiOral tissues consist of normal, human-derived epithelial cells, which have been cultured to form multilayered, highly differentiated models of the human buccal phenotypes.

Example 1

A dissolvable film for treating halitosis and/or dry mouth according to the invention was prepared by combining components described in Tab. 1. FC Brighter Flavor is a Colgate product comprising menthol.

TABLE 1

Ingredients for an oral mucoadhesive film for treating halitosis or dry mouth.

| Ingredient | Manufacturer | mass (g) | dry wt % |
| --- | --- | --- | --- |
| Propylene Glycol | Dow Chemical | 20.0 | 18.4 |
| PEG 400 | Dow Chemical | 15.0 | 13.8 |
| FC Brighter Flavor | Colgate | 18.1 | 16.7 |
| Sucralose | Colgate | 0.7 | 0.6 |
| Acetone | Spectrum | 80 | |
| Ethanol | Spectrum | 80 | |
| Purified Water | | 140 | |
| HPMC E5 | JRS Pharma | 28.0 | 25.8% |
| Xanthan Gum | Colgate | 11.6 | 10.7 |
| CMC Type 12 | Colgate | 11.6 | 10.7 |
| Carbopol 971P | Colgate | 3.65 | 3.4 |
| Total | | 408.65 | 100.0 |

Example 2

A dissolvable film for treating dry mouth according to the invention was prepared by combining components described in Tab. 2. Optaflow is a Symrise product comprising a plant-based saliva stimulator.

TABLE 2

Ingredients for an oral mucoadhesive film for treating dry mouth.

| Ingredient | Manufacturer | mass(g) | dry wt % |
| --- | --- | --- | --- |
| Propylene Glycol | Dow Chemical | 20.0 | 18.4% |
| PEG 400 | Dow Chemical | 15.0 | 13.8% |
| FC Brighter Flavor | Colgate | 18.0 | 16.6% |
| Sucralose | Colgate | 0.70 | 0.6% |
| Acetone | Fisher | 80 | |
| Ethanol | Sigma-Aldridge | 80 | |
| Purified Water | | 140 | |
| HPMC E5 | JRS Pharma | 28.0 | 25.8% |
| Xanthan Gum | Colgate | 11.6 | 10.7% |
| CMC Type 12 | Colgate | 11.6 | 10.7% |
| Optaflow M | Symrise | 3.6 | 3.3% |
| Total | | 408.50 | |

Example 3

A dissolvable film for treating dry mouth according to the invention was prepared by combining components described in Tab. 3.

TABLE 3

Ingredients for an oral mucoadhesive film for treating dry mouth.

| Ingredient | Manufacturer | mass(g) | dry wt % |
| --- | --- | --- | --- |
| Propylene Glycol | Dow Chemical | 20.0 | 17.5% |
| PEG 400 | Dow Chemical | 4.8 | 4.2% |
| FC Brighter Flavor | Colgate | 19.0 | 16.6% |
| Sucralose | Colgate | 0.80 | 0.7% |
| Acetone | Fisher | 75 | |
| Ethanol | Sigma-Aldrich | 75 | |
| Purified Water | | 135 | |
| HPMC E5 | JRS Pharma | 27.0 | 23.6% |
| Xanthan Gum | Colgate | 12.0 | 10.5% |
| CMC Type 12 | Colgate | 12.0 | 10.5% |
| Coconut Oil | Colgate (Ultimate92) | 19.0 | 16.6% |
| Total | | 399.60 | 100.00 |

Example 4

A dissolvable film for supporting dentures according to the invention was prepared by combining components described in Tab. 4.

TABLE 4

Ingredients for an oral mucoadhesive film for managing implications associated with dentures problems and/or for supporting dentures.

| Ingredient | Manufacturer | mass(g) | dry wt % |
| --- | --- | --- | --- |
| Propylene Glycol | Dow Chemical | 33.0 | 30.30% |
| PEG 400 | Dow Chemical | 20.0 | 18.40% |
| FC Brighter Flavor | Colgate | 4.0 | 3.70% |
| Sucralose | Colgate | 0.7 | 0.60% |
| Acetone | Fisher | 80 | |
| Ethanol | Sigma-Aldrich | 80 | |
| Purified Water | | 130 | |
| HPMC E5 | JRS Pharma | 28.0 | 25.70% |
| Xanthan Gum | Colgate | 11.6 | 10.70% |
| CMC Type 12 | Colgate | 11.6 | 10.70% |
| Total | | 398.9 | 100% |

Example 5

A dissolvable film for supporting dentures according to the invention was prepared by combining components described in Table 5 below.

Film Preparation Method

All of the water soluble ingredients were mixed is water until dissolved, thereby providing an aqueous phase. All of the organic soluble ingredients were mixed in ethanol and acetone (in a weight ratio of about 1:1) until dissolved, thereby providing an organic phase. The aqueous phase was gradually mixed into the organic phase. Mixing was continued until a significant increase in viscosity was observed (visual observation). The resulting viscous solution was casted to a thickness of about 0.1-0.3 mm onto a release liner, and was allowed to dry spontaneously in ambient conditions. Once dried, the prepared film was cut according to the required size (usually between 16-22 m) and shape (usually circular) and packaged.

TABLE 5

Ingredients for an oral mucoadhesive film for managing implications associated with dentures and/or for supporting dentures.

| Ingredient | dry % | mass (gr.) |
| --- | --- | --- |
| Propylene Glycol | 28.25% | 18.7 |
| PEG 400 | 17.40% | 11.5 |
| F Brighter flavor | 3% | 2 |
| Sucralose | 0.60% | 0.4 |
| Allura red AC | 0.04% | 0.03 |
| Cetalkonium chloride | 0.01% | 0.006 |
| Choline Salicylate | 8.70% | 5.7 |
| Acetone | | 44 |
| Ethanol | | 44 |
| Purified Water | | 78 |
| Methocel E5 | 22.80% | 15 |
| Xanthan Gum | 9.60% | 6.3 |
| CMC type 12 | 9.60% | 6.3 |
| Total | 100.00% | 239.93 |

The prepared film was cut into circular sections, each having a diameter of about 16 mm, such that each section contained about 4.35 mg of Choline Salicylate and 0.05 mg Cetalkonium chloride.

The physical properties of the film obtained are presented below in Table 6.

TABLE 6

Physical properties of the film prepared according to Example 5

| Test | Method | Acceptance limit | Results |
| --- | --- | --- | --- |
| 1 weight | Analytical balance | 50 ± 10 mg | 50 ± 10 mg |
| 2 thickness | Thickness gauge | 0.25 ± 0.05 mm | 0.2 ± 0.02 mm |
| 3 appearance | | pinkish film 16 mm diameter, flexible and homogenous | Conforms |
| 4 dissolution time | a film immersed in 50 ml PBS solution at 37° C. | | 2 hrs |
| 5 Yield | | | 170 films prepared |

Example 6

A dissolvable film for supporting dentures according to the invention was prepared by combining components described in Table 7 below. The film was prepared using the same method as described in Example 5.

TABLE 7

Ingredients for an oral mucoadhesive film for managing dentures problems and/or for supporting dentures

| Ingredient | dry % | mass (gr.) |
|---|---|---|
| Propylene Glycol | 25.25% | 16.7 |
| PEG 400 | 15.40% | 10.16 |
| F Brighter flavor | 3% | 2 |
| Sucralose | 0.60% | 0.4 |
| Allura red AC | 0.04% | 0.03 |
| Cetalkonium chloride | 0.01% | 0.006 |
| Choline Salicylate | 8.70% | 5.7 |
| Acetone | | 44 |
| Ethanol | | 44 |
| Purified Water | | 78 |
| Methocel E5 | 25.60% | 16.9 |
| Xanthan Gum | 10.70% | 7 |
| CMC type 12 | 10.70% | 7 |
| Total | 100.00% | 239.89 |

The prepared film was cut into circular sections, each having a diameter of 16 mm, such that each section contained about 4.78 mg of Choline Salicylate and 0.055 mg Cetalkonium chloride.

The physical properties of the film obtained are presented below in Table 8.

TABLE 8

Physical properties of the film prepared according to Example 6

| Test | Method | Acceptance limit | Results |
|---|---|---|---|
| 1 weight | Analytical balance | 50 ± 10 mg | 55 ± 5 mg |
| 2 thickness | Thickness gauge | 0.25 ± 0.05 mm | 0.25 ± 0.02 mm |
| 3 appearance | | pinkish film 16 mm diameter, flexible and homogenous | Conforms |
| 4 dissolution time | a film immersed in 50 ml PBS solution at 37° C. | | More than 4 hrs |
| 5 yield | | | 200 films |

While the invention has been described using some specific examples, many modifications and variations are possible. It is therefore understood that the invention is not intended to be limited in any way, other than by the scope of the appended claims.

The invention claimed is:

1. A dissolvable film adapted to adhere to an oral mucosal tissue of a subject and provide denture support, wherein said film comprises:
   i) at least three indigestible hydrophilic polymers constituting from 35% to 55% of the film dry weight;
   ii) a polyacrylic acid polymer; and
   iii) active ingredients comprising between 4.0-5.0 mg choline salicylate and between 0.03-0.07 mg cetalkonium chloride;
      wherein said at least, three indigestible hydrophilic polymers comprise xanthan gum and carboxymethyl cellulose (CMC) in a weight ratio of between 1:0.8-1.6 constituting from 15% to 25% of the film dry weight, and hydroxypropyl methylcellulose (HPMC) present in amount of 10% to 40% of the film dry weight; and
      wherein the film has a dissolution time in an oral cavity of 1 to 8 hours;
      wherein the film is adapted to be positioned between a subject's gums and denture to reduce pressure of the denture on the subject's gums.

2. The film of claim 1, further comprising plasticizers in an amount of from 25% to 50% of the film dry weight.

3. The film of claim 1, further comprising an additive in an amount up to 4% of the film dry weight, the additive. being selected from the group consisting of additional active agents, polymers adjusting the hydrophobicity of the polymer structure of said film, permeation enhancers, sweeteners, taste-masking agents, taste or flavor modifiers, plasticizers, release modifiers, pH-adjusting agents or buffering agents, preservatives or stabilizers, complexing agents, coloring agents, and emulsifying agents.

4. The film of claim 1, having a thickness of up to 0.8 mm.

5. A film adapted to adhere to an oral mucosal tissue of a subject and, provide denture support, wherein said film comprises:
   i) at least three indigestible hydrophilic polymers constituting from 35% to 55% of the film dry weight;
   ii) a polyacrylic acid polymer; and
   iii) active ingredients comprising between 4.0-5.0 mg choline salicylate and between 0.03-0.07 mg cetalkonium chloride;
      wherein said at least three indigestible hydrophilic polymers comprise xanthan gum and carboxymethyl cellulose (CMC) in a weight ratio of between 1:0.8-1.6 constituting from 15% to 25% of the film dry weight and hydroxypropyl methylcellulose (HPMC) present in amount of 10% to 40% of the film dry weight; and having a dissolution time in the oral cavity of 8 hours or more, and wherein the film is adapted to be positioned between a subject's gums and denture to reduce pressure of the denture on the subject's gums.

* * * * *